United States Patent [19]

Houlihan et al.

[11] 3,994,961

[45] *Nov. 30, 1976

[54] 10-(2-SUBSTITUTED-AMINO-ETHYL)-10,11-DIHYDRO-5-METHYLENE-5H-DEBENZO[a,d]CYCLOHEPTENES

[75] Inventors: William J. Houlihan, Mountain Lakes; Jeffrey Nadelson, Lake Parsippany, both of N.J.

[73] Assignee: Sandoz, Inc., E. Hanover, N.J.

[ * ] Notice: The portion of the term of this patent subsequent to Dec. 9, 1992, has been disclaimed.

[22] Filed: Feb. 13, 1974

[21] Appl. No.: 442,078

Related U.S. Application Data

[63] Continuation-in-part of Ser. No. 383,919, July 30, 1973, abandoned, which is a continuation-in-part of Ser. No. 368,652, June 11, 1973, abandoned, which is a continuation-in-part of Ser. No. 342,844, March 19, 1973, abandoned, which is a continuation-in-part of Ser. No. 325,909, Jan. 22, 1973, abandoned, which is a continuation-in-part of Ser. No. 308,302, Nov. 20, 1972, abandoned, which is a continuation-in-part of Ser. No. 224,323, Feb. 7, 1972, Pat. No. 3,925,476.

[52] U.S. Cl. ............... 260/501.1; 260/343.2 R; 260/348 R; 260/448.2 R; 260/470; 260/518 R; 260/518 A; 260/519; 260/501.21; 260/345.2; 260/551 R; 260/469; 260/570.8 TC; 260/558 A; 260/558 D; 260/570.5 CA; 424/316; 424/330

[51] Int. Cl.² ......................................... C07C 87/29
[58] Field of Search ............... 260/570.5 CA, 501.1, 260/570.8 TC; 383/919

[56] References Cited

UNITED STATES PATENTS

| 3,409,640 | 11/1968 | Caldwell | 260/501.1 |
| 3,649,692 | 3/1972 | Humber | 260/501.1 X |
| 3,658,815 | 4/1972 | Fouche | 260/501.1 |

FOREIGN PATENTS OR APPLICATIONS

| 684,514 | 12/1968 | South Africa | 260/501.1 |

*Primary Examiner*—James O. Thomas, Jr.
*Assistant Examiner*—G. Breitenstein
*Attorney, Agent, or Firm*—Gerald D. Sharkin; Robert S. Honor

[57] ABSTRACT

10-(2-substituted-aminoethyl)-10,11-dihydro-5-methylene-2 or 3 7 or 8-substituted or unsubstituted-5H-dibenzo[a,d]cycloheptenes e.g., 10-(2-dimethylaminoethyl)-10,11-dihydro-5-methylene-5H-dibenzo[a,d]cycloheptane, prepared by various methods including acid dehydration of the corresponding dibenzo[a,d]cycloheptene-5-ols. The compounds are useful as anti-depressants.

5 Claims, No Drawings

10-(2-SUBSTITUTED-AMINO-ETHYL)-10,11-DIHYDRO-5-METHYLENE-5H-DEBENZO[a,d] CYCLOHEPTENES

This application is a continuation-in-part of copending application Ser. No. 383,919, filed July 30, 1973, now abandoned, which in turn is a continuation-in-part of copending application Ser. No. 368,652, filed June 11, 1973, now abandoned, which in turn is a continuation-in-part of copending application Ser. No. 342,844, filed Mar. 19, 1973, now abandoned, which in turn is a continuation-in-part of copending application Ser. No. 325,909, filed Jan. 22, 1973, now abandoned, which in turn is a continuation-in-part of copending application Ser. No. 308,302, filed Nov. 20, 1972, now abandoned, which in turn is a continuation-in-part of copending application Ser. No. 224,323, filed Feb. 7, 1972 now U.S. Pat. No. 3,925,476.

This invention relates to 5-methylene-5H-dibenzo[a,d]cycloheptenes. More particularly, it relates to 10-(2-substituted aminoethyl)-10,11-dihydro-5-methylene-2 or 3, 7 or 8-substituted or unsubstituted-5H-dibenzo[a,d]cycloheptenes, acid addition salts thereof, intermediates thereof, and processes for their preparation.

The compound of this invention may be represented by the following structural formula:

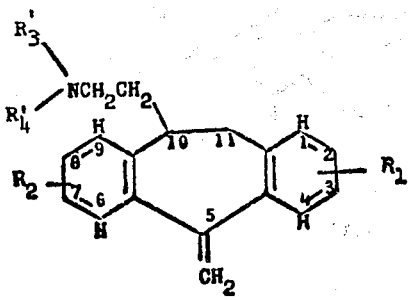

(I)

wherein
$R_1$ and $R_2$ each independently represent hydrogen or fluoro, and
$R_3$ and $R_4$ are each independently lower alkyl having 1 to 2 carbon atoms, i.e., methyl or ethyl, or one of $R_3'$ and $R_4'$ is hydrogen and the other is methyl.

The compounds of formula (I) having the following structural formula are preferred

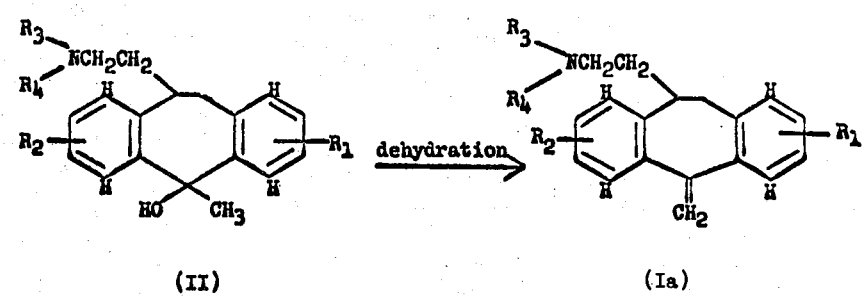

(Ip)

$R_1$ and $R_2$ are as defined above.

A preferred aspect of the invention is the compound 10-(2-dimethylaminoethyl)-10,11-dihydro-5-methylene-5H-dibenzo[a,d]cycloheptene and 10-(2-dimethylaminoethyl)-10,11-dihydro-7-fluoro-5-methylene-5H-dibenzo[a,d]cycloheptene and pharmaceutically acceptable acid addition salts thereof.

The compounds of formula (I) in which $R_3'$ and $R_4'$ are lower alkyl as previously defined may be prepared by the following reaction scheme A:

wherein
$R_1$ and $R_2$ have the above stated significance and
$R_3$ and $R_4$ represent said lower alkyl.

The compounds of formula (Ia) may be prepared by treating a novel compound of formula (II) with a dehydrating agent such as dilute or concentrated mineral acids e.g. sulfuric acid, hydrochloric acid and the like, iodine, phosphorus oxychloride, or thionyl chloride, an alkyl or arylsulfonyl chloride such as methanesulfonyl chloride or benzenesulfonyl chloride or an inorganic acid or Lewis acid used in the solid form. Examples of the last two acid types are potassium bisulphate, boric acid, aluminum oxide, and silicon dioxide. When phosphorus oxychloride or thionyl chloride or an alkyl or arylsulfonyl chloride is used as the dehydrating agent, it is preferred that an acid binding agent such as a lower alkyl tertiary amine wherein alkyl is defined as having 1 to 4 carbon atoms, e.g. triethylamine, be used. The reaction utilizing these dehydrating agents as well as that using the solid inorganic acids and Lewis acids may be conveniently carried out in inert hydrocarbons such as benzene, toluene and the like, at a temperature from about 50° C. to the reflux temperature of the reaction medium, preferably the reflux temperature, for about 1 to 24 hours, preferably 1 to 4 hours. The preferred dehydration medium is 1M to 5M sulfuric acid. Neither the solvents nor the temperatures used are critical.

The compounds of formula (II) may be prepared by the following reaction scheme B:

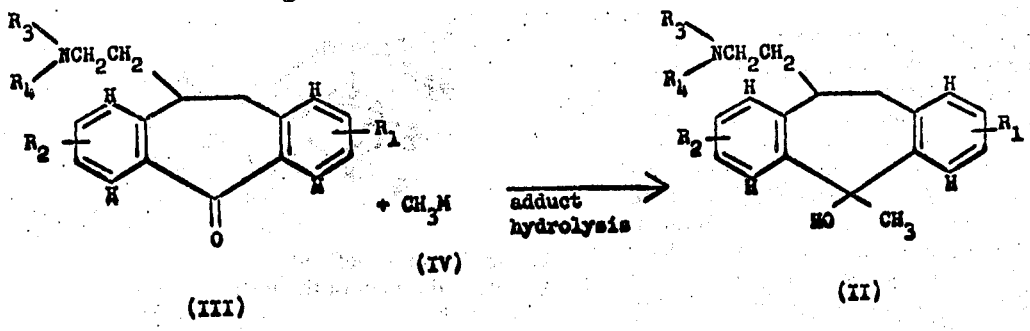

wherein
R₁, R₂, R₃ and R₄ have the above stated significance, and
M is Li or MgY,
wherein
Y is halo having an atomic weight of 35 to 127.

The compounds of formula (II) may be prepared by treating a compound of formula (III) with an organometallic reagent of formula (IV), e.g. methyllithium, and the like, in the presence of an inert atmosphere, e.g. nitrogen gas, in an inert solvent, such as diethyl ether, tetrahydrofuran, benzene, toluene and the like. When M is Li, at a temperature of from −20° to +25° C., preferably −5° to +5° C. for about 5 to 45 minutes, preferably 10 to 20 minutes. When M is MgY at a temperature of 10° to 20° C, for about 1 to 6 hours, preferably 3 to 5 hours, followed by standard hydrolysis of the resulting adduct, e.g., water or aqueous ammonium chloride solution. Neither the solvents nor the temperatures used are critical, The compounds of formula (III) are a further aspect of this invention and may be prepared by the following reaction scheme C:

phosphoric acid, polyphosphoric acid and the like. When a Lewis acid is used, the reaction may be carried out in an inert solvent such as dichloromethane, carbon tetrachloride, carbon disulfide, nitrobenzene and the like. A solvent is not necessary when a strong mineral acid is used but solvents such as those employed for the Lewis acid may be utilized. The cyclization may be carried out at a temperature from about 20° C. to 150° C., preferably from about 200° C. to about 120° C., for about 2 to 10 hours preferably for about 3 to 6 hours. The reaction may also be run at 140° C. overnight which is preferred in the preparation of the compound where R₂ is fluorine, e.g. 10-(2-dimethylaminoethyl)-10.11-dihydro-7-fluoro-5H-dibenzo[a,d]cyclohepten-5-one and acid addition salts thereof. Neither the solvents nor the temperatures used are critical.

When using a Lewis acid, compound (V) may optionally be used in the form of the corresponding acid chloride. The acid chloride of compound (V) may be prepared by conventional techniques, e.g. treating compound (V) with thionyl chloride in a solvent such as methylene chloride. The straight chain 1-4 carbon alkyl esters of the acid (V), prepared therefrom by

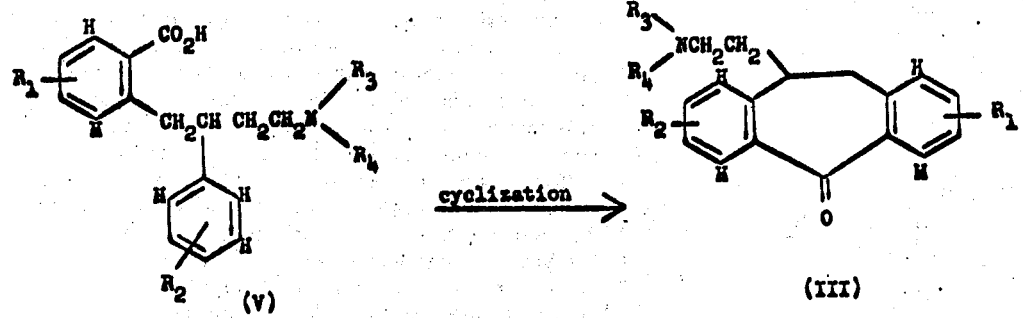

wherein
R₁, R₂, R₃ and R₄ have the above stated significance.

The compounds of formula (III) may be prepared by cyclization of a compound of formula (V) in a strong Lewis acid medium such as stannic tetrachloride, ferric chloride, titanium 100°and the like, or in strong mineral acid medium such as concentrated sulfuric acid, conventional techniques, may optionally be utilized in place of the corresponding acid, and otherwise under the same conditions described above to obtain compounds (III).

As a further aspect of their invention, the compounds of formula (Ia) may also be prepared by the following reaction scheme D:

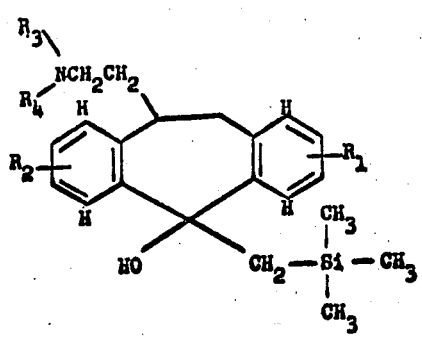

(VI)

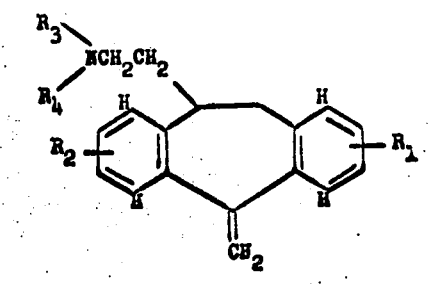

(Ia)

wherein $R_1$, $R_2$, $R_3$ and $R_4$ have the above stated significance.

The compounds of formula (Ia) may be prepared by treating a compound of formula (VI) with sodium hydride in the presence of an inert organic solvent such as diethyl ether, hexane, heptane or tetrahydrofuran, the latter being especially preferred. The temperature of the reaction is not critical but it is preferred that the reaction be carried out at temperatures between about $-10°$ to $+10°$ C., especially $-5°$ to $+5°$ C. The reaction may be run for 2 to 10 hours, preferably 4 to 6 hours. The particular solvent used and the reaction time are not critical.

The compounds of formula (VI) are prepared by the following reaction scheme E:

$R_1$, $R_2$, $R_3$ and $R_4$ have the above stated significance.

The compounds of formula (VI) are prepared by treating a compound of the formula (III) with a Grignard reagent of the formula (VII) in the presence of an inert organic solvent such as tetrahydrofuran, heptane, hexane, or diethylether, the latter being especially preferred. The temperature of the reaction is not critical, but it is preferred that the reaction be carried out at the reflux temperature of the solvent. The reaction may be run for 2 to 10 hours, preferably 4 to 6 hours, followed by standard hydrolysis of the resulting adduct, preferably with aqueous ammonium chloride. Neither the solvents nor the reaction times used are critical.

The compounds of formula (Ia) may also be prepared by another inventive process as represented by the following reaction scheme F:

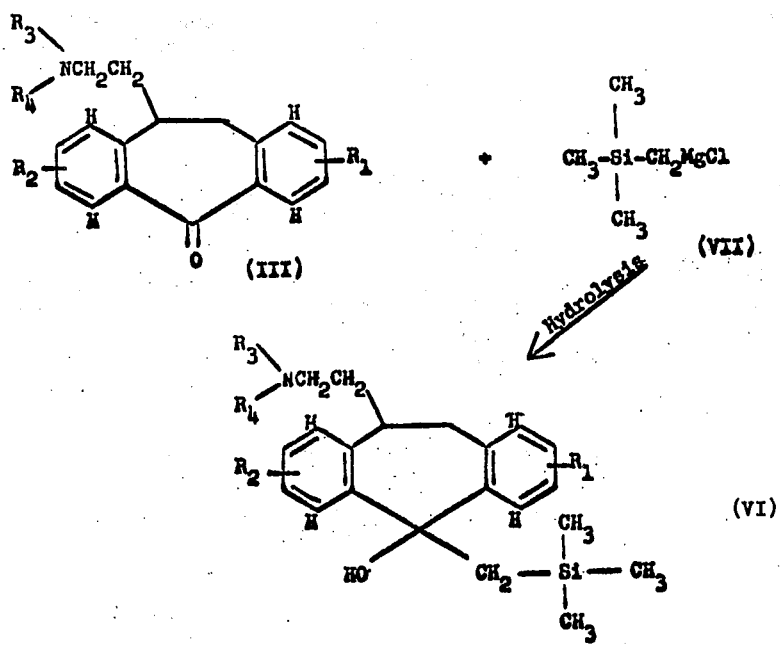

where

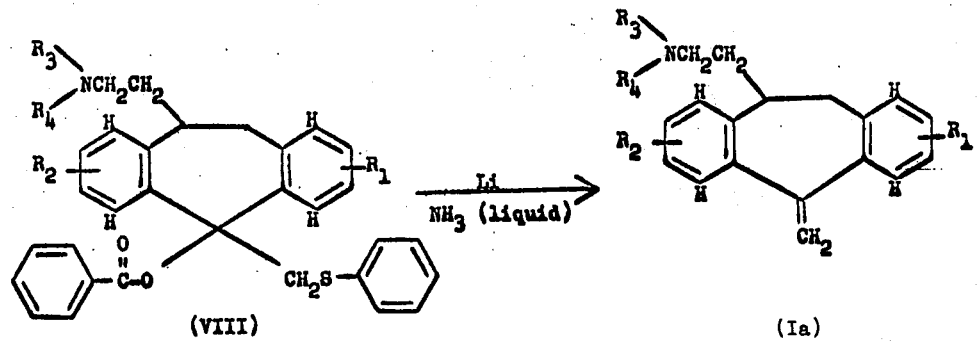

where
R₁, R₂, R₃ and R₄ have the above stated significance.

The compound of formula (Ia) are prepared by treating a compound of the formula (VIII) with lithium in the presence of liquid ammonia and in the presence of an inert atmosphere, e.g. nitrogen, helium, or argon at the reflux temperature of the system. Although a solvent is unnecessary, it is preferred that the reaction be carried out in the presence of an inert organic solvent such as tetrahydrofuran or diethylether, the latter being inert organic solvent, such as tetrahydrofuran, heptane, hexane or diethylether, the latter being especially preferred. The temperature of the reaction is not critical, but it is preferred that the reaction be carried out at temperatures between about 10° to 40° C., especially from about 20° to 30°. Although the reaction time is not critical, it is preferred that the reaction be run from about 1 to 5 hours, preferably from about 2 to 3 hours.

The compounds of formula (IX) are prepared according to the following reaction scheme H:

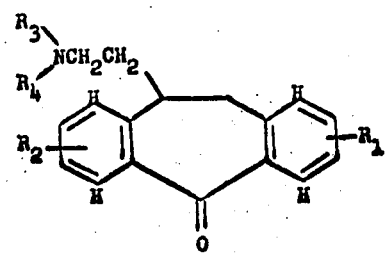

(III)

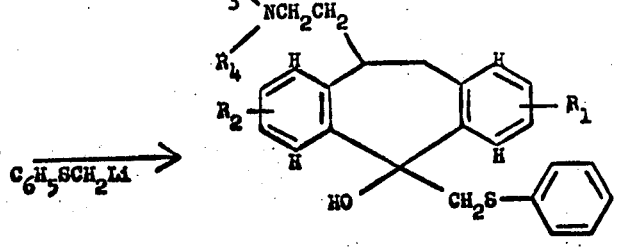

(IX)

especially preferred. The temperature of the reaction is not critical, but it is preferred that the reaction be carried out at the reflux temperature of the system. Although the reaction time is not critical, it is preferred that the reaction be run from about 15 to 45 minutes, especially 25 to 35 minutes.

The compounds of formula (VIII) are prepared according to the following reaction scheme G:

where
R₁, R₂, R₃ and R₄ have the above stated significance.

The compounds of formula (IX) are prepared by treating a compound of the formula (III) with phenylthiomethyllithium under an inert atmosphere such as nitrogen, helium, or argon in the presence of an inert organic solvent such as diethylether, heptane, hexane or tetrahydrofuran, the latter being especially preferred. The temperature of the reaction is not critical,

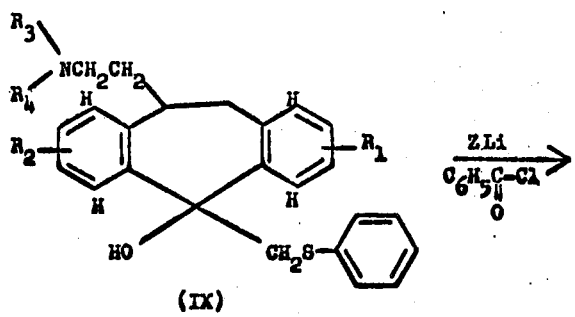

(IX)

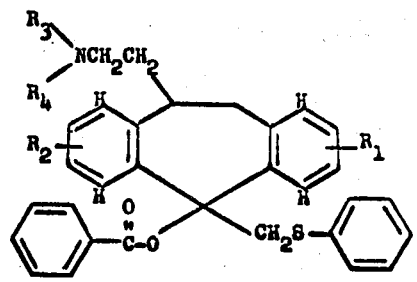

(VIII)

where
Z is alkyl having 1 to 4 carbon atoms, and
R₁, R₂, R₃ and R₄ have the above stated significance.

The compounds of formula (VIII) are prepared by treating a compound of formula (IX) with an alkyl lithium such as butyllithium in liquid ammonia under nitrogen atmosphere at reflux temperature of the system followed by benzoyl chloride in the presence of an but it is preferred that the reaction be carried out at temperatures between about 10° to 40° C. especially from about 20° to 30° C. The reaction may be run from about 15 to 30 hours; preferably from about 20 to 25 hours.

According to a still further aspect of this invention, the compounds of formula (Ia) may be prepared according to the following reaction scheme J:

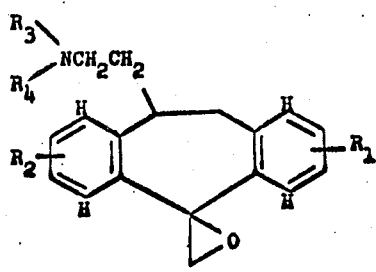

(X)

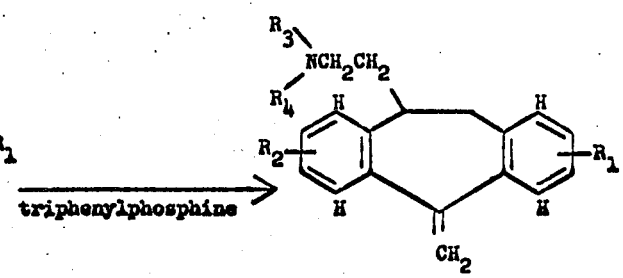

(Ia)

where
R₁, R₂, R₃ and R₄ have the above stated significance.

The compounds of formula (Ia) may be prepared by treating a compound of the formula (X) with triphenylphosphine optionally in an inert organic solvent such as tetrahydrofuran, benzene, toluene or the like, tetrahydrofuran being sepecially preferred. The temperature of the reaction is not critical but it is preferred that the reaction be carried out at temperatures from about 160° to 200° C., preferably 175° to 185° C. The reaction may be run from about 3 to 8 hours, preferably 4 to 6 hours.

The compounds of formula (X) are prepared according to the following reaction scheme K:

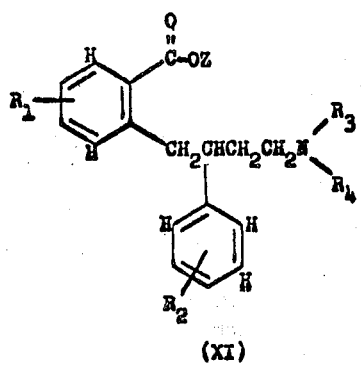

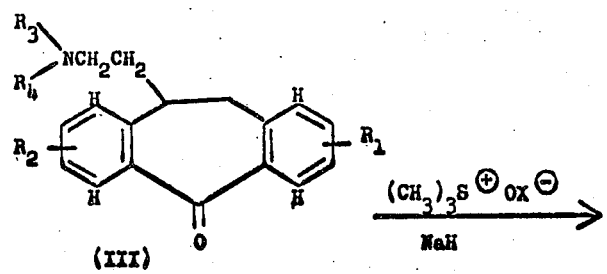

where
X is halo having an atomic weight from about 35 to 80, and
R₁, R₂, R₃ and R₄ have the above stated significance.

The compounds of formula (X) are prepared by treating a compound of formula (III) with trimethyloxosulfonium halide such as trimethyloxosulfonium iodide followed by sodium hydride in the presence of dimethyl sulfoxide. The temperature of the reaction is not critical and it is preferred that the reaction be carried out at temperatures from about 10° to 60° C., preferably 20° to 50° C. Although the reaction time is not critical, it is preferred that the reaction be run from about 10 minutes to 2 hours, preferably 15 minutes to 1.5 hours.

The compounds of formula (Ia) as an additional aspect to this invention are prepared according to the following reaction scheme L:

where
R₁, R₂, R₃ and R₄ have the above stated significance.

The compounds of formula (Ia) are prepared by treating a compound of the formula (III) with methyltriphenylphosphonium bromide followed by sodium hydride in the presence of dimethyl sulfoxide. Although the temperature of the reaction is not critical, it is preferred that the reaction be carried out at temperatures from about 10° to 40° C., preferably 20° to 30° C. The reaction may be run from about 30 minutes to 1.5 hours.

The compounds of formula (III) may also be prepared according to the following reaction scheme M:

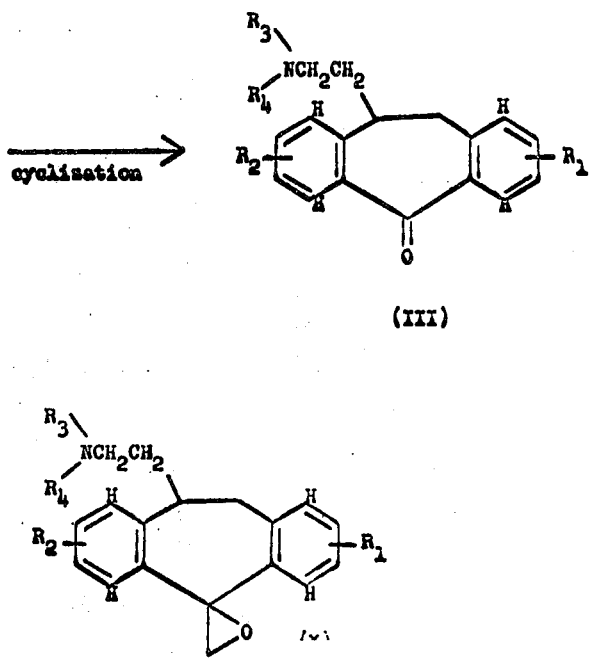

where
R₁, R₂, R₃, R₄ and Z have the above stated significance.

The compounds of formula (III) may be prepared by cyclization of a compound of the formula (XI) in a strong mineral acid such as concentrated sulfuric acid, phosphoric acid or polyphosphoric acid, the latter being preferred. The reaction may be carried out in an inert solvent such as dichloromethane, carbon disulfide, or carbon tetrachloride, preferably carbon tetrachloride. The cyclization may be carried out at a temperature from about 20° to 150° C., preferably from about 110° to 130° C. The reaction may be run from about 2 to 10 hours, preferably from about 5 to 7 hours. Neither the solvents, times nor the temperatures used are critical.

The compounds of formula (XI) are prepared according to the following reaction scheme N:

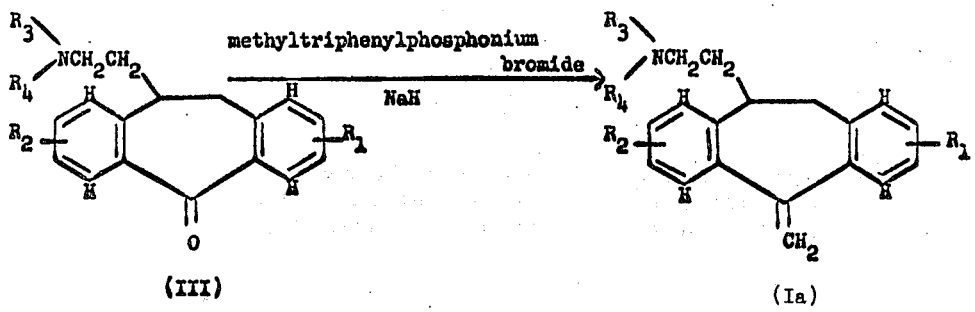

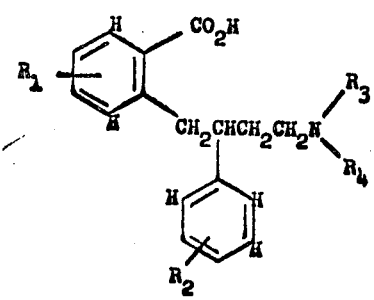

(V)

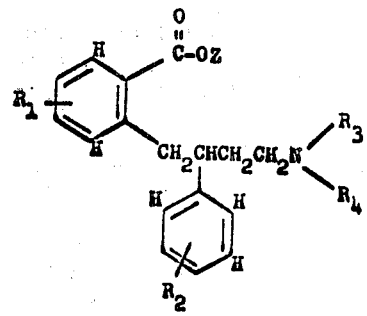

(XI)

where
R₁, R₂, R₃, R₄ and Z have the above stated significance.

The compounds of formula (XI) are prepared by reacting a compound of the formula (V) with a non-aqueous mineral acid such as gaseous hydrogen chloride or concentrated sulfuric acid in the presence of an inert organic solvent such as the 1-4 carbon alkanols, e.g. methanol, ethanol and the like. Although the temperature of the reaction is not critical, it is preferred that the reaction be run from about 20° to 60° C., preferably the reflux temperature of the solvent. The reaction may be run from about 12 to 24 hours, preferably 17 to 19 hours.

The compounds of formula (V) may be prepared by the following reaction scheme P:

presence of a noble metal catalyst such as palladium, platinum, rhodium and the like, optionally neat or on a support such as charcoal, at an atmosphere of from 35 to 100 psi preferably 50 to 55 psi, in an inert lower alkanol having 1 to 4 carbon atoms, such as methanol, ethanol, propanol, isopropanol, butanol, isobutanol, or an acetic acid, at a temperature of from 20° to 80° C. preferably 25° to 35° C., until one equivalent amount of hydrogen is absorbed. To enhance the reaction, aqueous mineral acid such as hydrochloric acid, sulfuric acid, or perchloric acid may be added to the reaction medium. Neither the solvents, temperatures or pressures used are critical.

A further method of preparing compounds (V) by compounds (XII) is shown by the following reaction scheme Q:

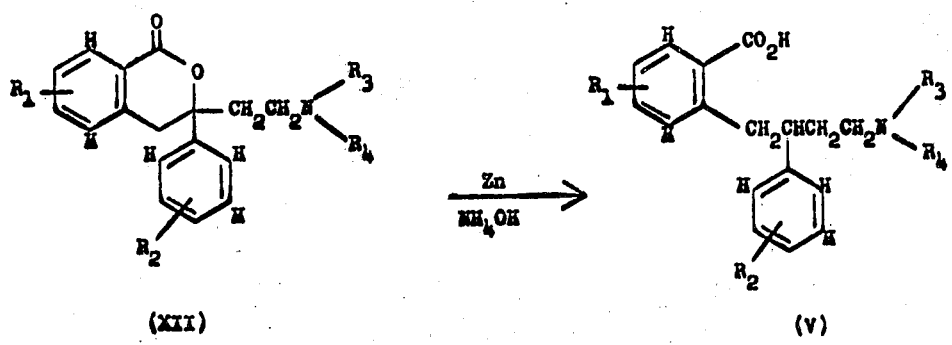

(XII)                                    (V)

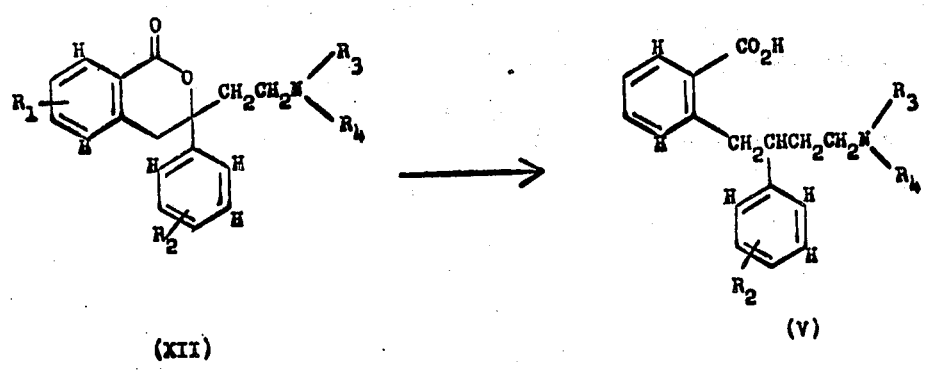

(XII)                    (V)

where
R₁, R₂, R₃ and R₄ have the above stated significance.

The compounds of formula (V) may be prepared by hydrogenating a compound of formula (XII) in the where
R₁, R₂, R₃ and R₄ have the above stated significance.

The compounds of formula (V) may be prepared according to reaction scheme Q by reducing a compound of formula (XII) using a zinc-ammonium hydroxide reduction system optionally in the presence of (XIV)     (XV)

cupric sulfate. Although the particular solvent used is not critical, it is preferred that the reaction be carried out in the presence of an inert organic solvent such as the lower alkanols, e.g. methanol, ethanol and the like, especially ethanol. The temperature of the reaction is not critical, but is is preferred that the reaction be carried out at temperatures from about 60° to 100° C., preferably 75° to 84° C. The reaction may be run from about 24 to 48 hours, preferably 28 to 30 hours.

The compounds of formula (XII) may be prepared by the following reaction scheme R:

(XIII)     (XII)

where $R_1$, $R_2$, $R_3$ and $R_4$ have the above stated significance, and $R_6$ represents lower alkyl, as previously defined.

The compounds of formula (XII) are prepared by heating a compound of formula (XIII) optionally in an inert solvent such as tetrahydrofuran, the hydrocarbons or halogenated hydrocarbons such as hexane, heptane, benzene, toluene, o-dichlorobenzene and the like, at about 60° to 220° C., preferably about 140° to 160° C. for about 15 to 48 hours, preferably about 20 to 28 hours. The temperatures and times used are not critical. To improve yields and obtain a better quality product, the reaction may be performed under inert atmosphere, e.g. nitrogen gas.

The compounds of formulas (I), (II), (III), (V), (VI), (VIII), (IX), and (X) may exist in the form of their acid addition salts. Said salts and their respective free bases may be converted from one to the other by conventional techniques and are chemically interchangeable for purposes or the above described processes.

The compounds of formula (XIII) may be prepared as indicated by the following reaction scheme S:

(XIII)

where $R_1$, $R_2$, $R_3$, $R_4$ and $R_6$ have the above stated significance.

The compounds of formula (XIII) are prepared by condensing a compound of formula (XIV) with a compound of formula (XV) in the presence of inert atmosphere, e.g. nitrogen gas, in an inert solvent such as diethyl ether, tetrahydrofuran, hexane, heptane, benzene and the like or mixtures thereof, and subjecting the reaction mixture to hydrolysis, preferably with aqueous ammonium chloride. The condensation may be carried out at a temperature of from −30° to −15° C., preferably −25° to −20 ° C. for about 1 to 3 hours. The hydrolysis is performed in conventional manner at a temperature of about −15° to −5 ° C. Neither temperatures, solvents nor hydrolyzing agents used are critical. Compound (XV) is preferably added in inert solvent to a cold (−30° C. to −15 ° C) inert solvent solution of compound (XIV).

Another aspect of this invention is the preparation of the compounds of formula (I) in which one of $R_3'$ and $R_4'$ is hydrogen and the other is methyl. These compounds may be prepared according to the following reaction scheme:

(XVI)     (Ib)

where $R_1$ and $R_2$ are as defined above.

The compounds of formula (Ib) are prepared by treating a compound of the formula (XVI) with an alkali metal hydroxide, such as potassium hydroxide, sodium hydroxide and lithium hydroxide, preferably potassium hydroxide in the presence of an inert organic solvent. Although the particular solvent used is not critical, it is preferred that the reaction be carried out in the presence of dimethylacetamide, dimethylformamide or the lower alkanols, e.g., methanol, ethanol and the like, preferably ethanol. The temperature of the reaction is not critical, but it is preferred that the reaction be run from about 80° to 150° C, preferably the reflux temperature of the solvent. The reaction is run from about 5 to 24 hours, preferably from about 8 to 12 hours.

The compounds of formula (XVI) may be prepared according to the following reaction scheme:

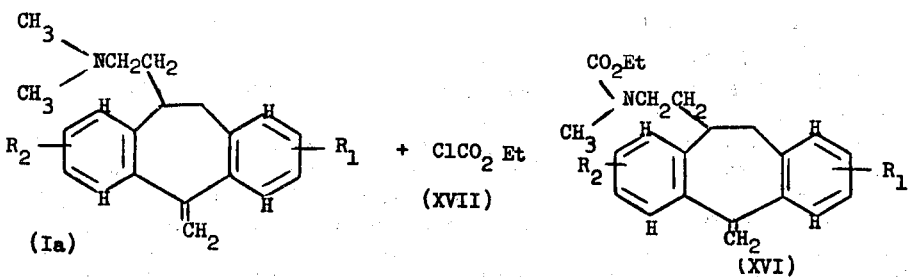

where
  Et represents ethyl and
  R₁ and R₂ are as defined above.

The compounds of formula (XVI) are prepared by treating a compound of the formula (Ia) with a compound of the formula (XVII) in the presence of an inert organic solvent. Although the particular solvent employed is not critical, it is preferred that the reaction be carried out in the presence of the aromatic hydrocarbons such as benzene, toluene, xylene and the like, preferably toluene. The temperature of the reaction is not critical, but it is preferred that the reaction be run from about 80 to −180° C, preferably the reflux temperature of the solvent. The reaction is run from about 12 to 48 hours, preferably from about 16 to 20 hours.

The compounds of formulas (I), (II), (III), (V), (VI), (VIII), (IX), (X), (XI), (XII) and (XVI) may be recovered using conventional techniques such as crystallization, evaporation, or filtration.

Certain of the compounds of formulas (IV), (VII), (XIV), (XV) and (XVII) are known and may be prepared by methods disclosed in the literature. Those compounds (IV), (VII), (XIV), (XVII) not specifically disclosed may be prepared by analogous methods from known materials.

It will be understood that certain of the compounds of formulas (I), (II) and (III) exist in racemic form or in the form of optically active isomers. The separation and recovery of the respective isomers may be readily accomplished employing conventional techniques and such isomers are included within the scope of this invention.

The compounds of formula (I) are useful because they posses pharmacological activity in animals. More particularly, the compounds of formula (I) are useful as anti-depressants agents as indicated by their activity in mice given intraperitoneally 0.1 to 25 mg/kg of body weight of active material, and tested by the method basically as described by Spencer, P. S. J., Antagonism of Hypothermia in the Mouse by Antidepressant Drugs, pp. 194–204, Ed. S. Garattini and M. N. O. Dukes, Excerpta Medica Foundation, 1967, and by their activity in the cat given typically 0.25–2.0 mg/kg of body weight of active material and tested for their effect on 5-hydroxytryptophan and 1-tryptophan induced spinal monosynaptic reflex transmission, basically as described by Anderson E. G. and Shibuya T., the Effects of 5-Hydroxytryptophan and 1-tryptophan on Spinal Synaptic Activity, pp. 352 to 360, J. of Pharm. and Exp. Therapeutics, Vol. 153, No. 2, 1966.

When so utilized, the compounds may be combined with one or more pharmaceutically acceptable carrier or adjuvants. They may be administered orally or parenterally and, depending upon the compound employed and the mode of administration, the exact dosage utilized may vary.

Furthermore, the compounds (I) may be similarly administered in the form of their non-toxic pharmaceutically acceptable acid addition salts. Such salts possess the same order of activity as the free base, are readily prepared by reacting the base with an appropriate acid and accordingly, are included within the scope of the invention. Representative of such salts are the mineral acid salts, such as the hydrochloride, hydrobromide, sulfate, phosphate and the like and the organic acid salts, such as succinate, benzoate, acetate p-toluenesulfonate, benzenesulfonate, maleate and the like.

As noted above, the compounds of formula (I) exist as optical isomers. In some cases, greater pharmacological activity or other beneficial attributes may be found for a particular isomer and in such instances, administration of such isomers may be preferred.

In general, satisfactory results are obtained when the compounds are administered as anti-depressents at a daily dosage of from about 0.5 to 100 milligrams per kilogram of animal body weight. This daily dosage is preferably given in divided doses, e.g., 2 to 4 times a day, or in sustained release form. For most large animals, the total daily dosage is from about 30 to 750 milligrams and dosage forms suitable for internal adminstration comprise from about 7.5 to 375 milligrams of the compound in admixture with a solid or liquid pharmaceutical carrier or diluent.

EXAMPLE 1

2-(β-[2-dimethylaminoethyl]-β-hydroxyphenethyl)-N-methylbenzamide

To a flask equipped with a stirrer, dropping funnel, condenser and gas inlet tube maintained under a nitrogen atmosphere there is added at room temperature 40.0 g. (0.28 mole) of o-methyl-N-methyl benzamide and 250 ml. of anhydrous tetrahydrofuran. The reaction flask is immersed in an ice bath and cooled to an internal temperature of 5° C. Stirring is initiated and 360 ml. of 1.6 M. n-butyllithium (0.616 mole) in hexane is added dropwise for about 1 hour maintaining the temperature below 8° C. The resulting red dilithio salt (compound VIII) is stirred at 5° C. for 1 additional hour and the reaction flask is then immersed in a dry-ice acetone bath and cooled to an internal temperature of −30° C. To the cold reaction mixture a solution of 49.7 g. (0.28 mole) 3-dimethylaminopropiophenone in 140 ml. anhydrous tetrahydrofuran is added dropwise in ca. 45 minutes maintaining the temperature between −30° C. and −20° C. The resulting reaction mixture is stirred at −25° C. for 1 hour, allowed to warm to −10° C. in ca. 1 hour, and then treated with 200 ml. of saturated aqueous ammonium chloride while maintaining the temperature below 0° C. The resulting solid is filtered, washed thoroughly with water and recrystallized from methylene chloride-ether (1:1) to give 2-(β-[2-dimethylaminoethyl]-β-hydroxyphenethyl)-N-methylbenzamide; m.p. 139.5 to 140.5° C.

When the above process is carried out and in place of o-methyl-N-methyl benzamide there is used
 a. 4-fluoro-N,2-dimethylbenzamide,
 b. N,2-dimethylbenzamide
 c. N,2-dimethylbenzamide,
 d. o-methyl-N-ethylbenzamide, or
 e. 4-fluoro-N,2-dimethylbenzamide,
and in place of 3-dimethylamino ropiophenone there is used,
 a. 4'-fluoro-3-dimethylaminopropiophenone,
 b. 4'-fluoro-3-dimethylpro iophenone,
 c. 3'-fluoro-3-dimethylpropio henone,
 d. 3-diethylaminopropiophenone, or
 e. 3-dimethylaminopropiophenone,
and reacting the correspondingly lettered benzamides and propiophenones, there is obtained,
 a. 4-fluoro-2-(4-fluoro-β-[2-dimethylaminoethyl]-βhydroxyphenethyl)-N-methylbenzamide, or
 b. 2-(4-fluoro-β-[2-dimethylaminoethyl]-μ-hydroxyphenethyl)-N-methylbenzamide
 c. 2-(3-fluoro-β-[2-dimethylaminoethyl[-β-hydroxyphenethyl)-N-methylbenzamide,
 c. 2-(β-[2-diethylaminoethyl]-β-hydroxyphenethyl-N-methylbenzamide, or
 e. 4-fluoro-2-(β-[2-dimethylaminoethyl]-β-hydroxyphenethyl)-N-methylbenzamide, respectively.

EXAMPLE 2

3-[2-dimethylaminoethyl]-3,4-dihydro-3-phenylisocoumarin

To a flask equipped with a stirrer, condenser and gas inlet tube maintained under a nitrogen atmosphere there is added at room temperature 16.3 g (0.05 mole) of 2-(β-[2-dimethylaminoethyl]-β-hydroxyphenethyl)-N-methylbenzamide and 170 ml of o-dichloro benzene. Stirring is initiated and the mixture is heated at reflux for 18 hours. The excess o-dichlorobenzene is then removed by distillation in vacuo and the resulting oil is crystallized from ether to give 3-[2-dimethylaminoethyl]-3,4-dihydro-3-phenylisocoumarin; m.p. 95.0°–95.5° C.

When the above process is carried out and in place of 2-(β-[2-dimethylaminoethyl]-β-hydroxyphenethyl)-N-methylbenzamide, there is used
 a. 4-fluoro-2-(4-fluoro-β-[2-dimethylaminoethyl]-β-hydroxyphenethyl)-N-methylbenzamide,
 b. 2-(4-fluoro-β-[2-dimethylaminoethyl]-β-hydroxyphenethyl)-N-methylbenzamide,
 c. 2-(3-fluoro-β-[2-dimethylaminoethyl]-β-hydroxyphenethyl)-N-methylbenzamide,
 d. 2-(β-[2-diethylaminoethyl]-β-hydroxyphenethyl)-N-methylbenzamide, or
 e. 4-fluoro-2-(β-[2-dimethylaminoethyl]-β-hydroxyphenyl)-N-methylbenzamide,
there is obtained
 a. 6-fluoro-3-(4-fluorophenyl)-3-(2-dimethylaminoethyl)-3,4 dihydroisocoumarin;
 b. 3-(4-fluorophenyl)-3-(2-dimethylaminoethyl)-3,4-dihydroisocoumarin,
 c. 3-(3-fluorophenyl)-3-(2-dimethylaminoethyl)-3,4-dihydroisocoumarin,
 d. 3-(2-diethylaminoethyl)-3,4-dihydro-3-phenylisocoumarin, or
 e. 6-fluoro-2-(2-dimethylaminoethyl)-3,4-dihydro-3-phenylisocoumarin, respectively.

EXAMPLE 3

10-(2-dimethylaminoethyl)-10,11-dihydro-5-methylene,5H-dibenzo[a,d] cycloheptene maleate Step a.

2-(β-[2-dimethylaminoethyl]phenethyl)benzoic acid hydrochloride

A solution of 14.75 g. (0.05 mole) of 3-(2-dimethylaminoethyl-3,4-dihydro-3-phenylisocoumarin in 150 ml. ethanol containing 1 g. 10% palladium on charcoal is hydrogenated at 50 psi and room temperature until one equivalent of hydrogen is absorbed. The mixture is filtered and evaporated to give the intermediate 2-(β-[2-dimethylaminoethyl]phenethyl) benzoic acid hydrochloride, m.p. 152° to 154° C.

Step b.

10-(2-dimethylaminoethyl)-10,11-dihydro-5H-dibenzo [a,d] cyclohepten-5-one hydrochloride A mixture of 14.75 g (0.05 mole) of 2-(β-[2-dimethylaminoethyl] phenethyl)benzoic acid hydrochloride and 150 g polyphosphoric acid is heated at 110° C for 6 hrs. allowed to cool and poured onto crushed ice with stirring. The resulting solution is cooled on ice and made basic by the addition of solid potassium hydroxide, and extracted with methylene chloride. The methylene chloride is washed with water, dried over anhydride magnesium sulfate and evaporated in vacuo. The residue is dissolved in isopropanol, and treated with gaseous hydrogen chloride. The resulting precipitate is filtered and recrystallized from isopropanol to give the intermediate 10-(2-dimethylaminoethyl)-10,11-dihydro-5H-dibenzo[a,d]cyclohepten-5-one hydrochloride, m.p. 188°-190° C.

Following the above procedure and using an equivalent amount of ferric chloride in place of polyphosphoric acid, there is obtained the identical product.

Similarly using ferric chloride and 2-(β-[2-dimethylaminoethyl]phenethyl)benzoic acid chloride in place of 2-(β-[2-dimethylaminoethyl] phenethyl)benzoic acid hydrochloride, the identical product is again obtained.

Following the above detailed procedure out using 16.3 g. of 2-(p[2-dimethylaminoethyl]phenethyl)benzoic acid ethyl ester in place of 14.75 g. of 2-(β-[2-dimethylaminoethyl]phenethyl)benzoic acid hydrochloride, there is obtained 10-(2-dimethylaminoethyl)-10,11-dihydro-5H-dibenzo[a,d] cyclohepten-5-one hydrochloride; m.p. 188° to 190° C.

Step c)

10-(2-dimethylaminoethyl)-10,11-dihydro-5-methyl-5H-dibenzo[a,d]cyclohepten-5-ol To a solution of 19.4 g. (0.07 mole) of 10-(2-dimethylaminoethyl)10,11-dihydro-5H-dibenzo[ad,]cyclohepten-5-one in 200 ml. diethylether, under nitrogen, cooled to −5° C. 70 ml. 1.5N methyllithium (0.105 mole) in diethylether is added dropwise with stirring, maintaining temperature below 0° C., 15 minutes after the addition is complete the reaction is quenched by the addition of 50 ml. saturated ammonium chloride solution. The organic layer is separated, extracted with saturated sodium chloride solution, dried over anhydrous magnesium sulfate and evaporated. The crystalline residue is recrystallized from methylenechloride-methanol 1:1 to give the intermediate 10-(2-dimethylaminoethyl)-10,11-dihydro-5-methyl-5H-dibenzo[a,d]cyclohepten-5-ol, m.p. 161.5° to 162° C.

Following the above procedure and using an equivalent amount of methylmagnesiumchloride in place of methyllithium at room temperature instead of 0° C. for 3 hours instead of 15 minutes, the identical product is again obtained.

Step d.
10-(2-dimethylaminoethyl)-10,11-dihydro-5-methylene-5H-dibenzo[(a,d)]cycloheptene-maleate A mixture of 8g (0.027 mole) of 10-(2-dimethylaminoethyl)-10,11-dihydro-5-methyl-5H-dibenzo[a,d]-cyclohepten-5-ol and 250 ml 2M-sulfuric acid is refluxed for 2 hrs. The mixture is cooled in ice and made basic by the addition of solid potassium hydroxide. The mixture is extracted with methylene chloride. The methylene chloride is washed with water, dried over anhyd. magnesium sulfate and evaporated in vacuo. The oily residue is distilled at 140° C/0.5mm and the distillate is dissolved in ethanol and treated with maleic acid. The precipitate is filtered and recrystallized from diethylether-ethanol 1:1 to give the product 10-(2-dimethylaminoethyl)-10,11-dihydro-5-methylene-5H-dibenzo[a,d]cycloheptene maleate. m.p. 171°–172° C.

1. Following the above procedure and using an equivalent amount of ferric chloride in place of sulfuric acid, there is obtained the identical product.

EXAMPLE 4

Step a.
Following the procedure of Example 3, step a)and in place of 3-(2-dimethylaminoethyl)-3,4-dihydro-3-phenylisocoumarin, and starting with;
- a. 3-(4-fluorophenyl)-3-(2-dimethylaminoethyl)-3,4-dihydro-6-fluoro isocoumarin,
- b. 3-(4-fluorophenyl)-3-(2-dimethylaminoethyl)-3,4-dihydroisocoumarin,
- c. 3-(3-fluorophenyl)-3-(2-dimethylaminoethyl)-3,4-dihydroisocoumarin,
- d. 3-(2-diethylaminoethyl)-3,4-dihydro-3-phenylisocoumarin, or
- e. 6-fluoro-3-(2-dimethylaminomethyl)-3,4-dihydro-3-phenylisocoumarin, the following intermediates are obtained,
- a. 4-fluoro-2-(β-[2-dimethylaminoethyl]-p-fluorophenethyl)benzoic acid hydrochloride,
- b. 2-(β-[2-dimethylaminoethyl]-p-fluorophenethyl)benzoic acid hydrochloride,
- c. 2-(β-[2-dimethylaminoethyl]-m-fluorophenethyl)benzoic acid hydrochloride,
- d. 2-(β-[2-diethylaminoethyl)benzoic acid hydrochloride, or
- e. 4-fluoro-2-(β-[2-dimethylaminoethyl])benzoic acid hydrochloride, respectively.

Step b.
Following the procedure of Example 3, step b) and in place of 2-(β-[2-dimethylaminoethyl]phenethyl)benzoic acid hydrochloride, and starting with the correspondingly lettered intermediate of step a) of this example, the following intermediates are obtained,
- a. 10-(2-dimethylaminoethyl)-10,11-dihydro-2,7-difluoro-5H-dibenzo[a,d]cyclohepten-5-one hydrochloride,
- b. 10-(2-dimethylaminoethyl)-10,11-dihydro-7-fluoro-5H-dibenzo[a,d]cyclohepten-5-one hydrochloride,
- c. 10-(2-dimethylaminoethyl)-10,11-dihydro-8-fluoro-5H-dibenzo[a,d]cyclohepten-5-one hydrochloride,
- d. 10-(2-diethylaminoethyl)-10,11-dihydro-5H-dibenzo[a,d]cyclohepten-5-one hydrochloride, or
- e. 10-(2-dimethylaminoethyl)-10,11-dihydro-2-fluoro-5H-dibenzo[a,d]cyclohepten-5-one hydrochloride, respectively.

Step c)
Following the procedure of Example 3, step c) and in the place of 10-(2-dimethylaminoethyl)-10,11-dihydro-5H-dibenzo[a,d]-cyclohepten-5-one hydrochloride, and starting with the correspondingly lettered intermediate of Step b) of this Example, the following intermediates are obtained:
- a. 10-(2-dimethylaminoethyl)-10,11-dihydro-2,7-difluoro-5-methyl-5H-dibenzo [a,d]cyclohepten-5-ol,
- b. 10-(2-dimethylaminoethyl)-10,11-dihydro-7-fluoro-5-methyl-5H-dibenzo[a,d]cyclohepten-5-ol,
- c. 10-(2-dimethylaminoethyl)-10,11-dihydro-8-fluoro-5-methyl-5H-dibenzo[a,d]cyclohepten-5-ol,
- d. 10-(2-diethylaminoethyl)-10,11-dihydro-5-methyl-5H-dibenzo[a,d]cyclohepten-5-ol, or
- e. 10-(2-dimethylaminoethyl)-10,11-dihydro-2-fluoro-5-methyl-5H-dibenzo[a,d]cyclohepten-5-ol, respectively.

Following the procedure of Example 3, Step a) and in place of 10-(2-dimethylaminoethyl)-10,11-dihydro-5-methyl-5H-dibenzo[a,d]cyclohepten-5-ol, and starting with the correspondingly lettered intermediate of Step c) of the example, the following products are obtained:
- a. 10-(2-dimethylaminoethyl)-10,11-dihydro-2,7-difluoro-5-methylene-5H-dibenzo[a,d]cycloheptene maleate,
- b. 10-(2-dimethylaminoethyl)-10,11-dihydro-7-fluoro-5-methylene-5H-dibenzo dibenzo[a,d]cycloheptene maleate,
- c. 10-(2-dimethylaminoethyl)-10,11-dihydro-8-fluoro-5-methylene-5H-dibenzo [a,d]cycloheptene maleate,
- d. 10-(2-diethylaminoethyl)-10,11-dihydro-5-methylene-5H-dibenzo[a,d]cycloheptene maleate, or
- e. 10-(2-dimethylaminoethyl)-10,11-dihydro-2-fluoro-5-methylene-5H-dibenzo[a,d]cycloheptene maleate, m.p. 140°–142° C., respectively.

The 10-(2-dimethylaminoethyl)-10,11-dihydro-5-methylene-5H-dibenzo[a,d]cycloheptene maleate and the 10-(2-dimethylaminoethyl)-10,11-dihydro-7-fluoro-5-methylene-5H-dibenzo[a,d]cycloheptene maleate are effective antidepressant agents when orally administered to an animal suffering from depression at a dosage of 100 mg. 4 times per day.

EXAMPLE 5

Step a.

10-(2-dimethylaminoethyl)-10,11-dihydro-5-trimethylsilylmethyl-5H-dibenzo[a,d]cyclohepten-5-ol A Grignard reagent is prepared by conventional techniques from 12.2 g. (0.1 mole) trimethylsilylmethyl chloride and 24.3 g. magnesium metal (0.1 atom) and 200 ml. ether. The resulting solution is treated with 27.9 g. (0.1 mole) of 10-(2-dimethylaminoethyl)-10,11-dihydro-5H-dibenzo[a,d]cyclohepten-5-one in 100 ml. ether. Stirring is initiated and the mixture is heated at reflux for 5 hours, then cooled in ice and hydrolyzed with 150 ml. of saturated ammonium chloride. The layers are separated and the ether dried over anhydrous magnesium sulfate and evaporated to give 10-(2-dimethylaminoethyl)-10,11-dihydro-5-trimethylsilylmethyl-5H-dibenzo[a,d]cyclohepten-5-ol.

Following the above procedure and using in place of 10-(2-dimethylaminoethyl)-10,11-dihydro-5H-dibenzo[a,d]cyclohepten-5-one an equivalent amount of
- a. 10-(2-dimethylaminoethyl)-10,11-dihydro-2,7-difluoro-5H-dibenzo[a,d]cyclohepten-5-one,
- b. 10-(2-dimethylaminoethyl)-10,11-dihydro-7-fluoro-5H-dibenzo[a,d]cyclohepten-5-one,
- c. 10-(2-dimethylaminoethyl)-10,11-dihydro-8-fluoro-5H-dibenzo[a,d]cyclohepten-5-one,
- d. 10-(2-diethylaminoethyl)-10,11-dihydro-5H-dibenzo[a,d]cyclohepten-5-one, or
- e. 10-(2-dimethylaminoethyl)-10,11-dihydro-2-fluoro-5H-dibenzo[a,d]cyclohepten-5-one, there is obtained
- a. 10-(2-dimethylaminoethyl)-10,11-dihydro-2,7-difluoro-5-trimethylsilylmethyl-5H-dibenzo[a,d]cyclohepten-5-ol,
- b. 10-(2-dimethylaminoethyl)-10,11-dihydro-7-fluoro-5-trimethylsilylmethyl-5H-dibenzo[a,d]cyclohepten-5-ol,
- d. 10-(2-dimethylaminoethyl)-10,11-dihydro-8-fluoro-5-trimethylsilylmethyl-5H-dibenzo[a,d]cyclohepten-5-ol,
- d. 10-(2-diethylaminoethyl)-10,11-dihydro-5-trimethylsilylmethyl-5H-dibenzo[a,d]cyclohepten-5-ol, or
- e. 10-(2-dimethylaminoethyl)-10,11-dihydro-2-fluoro-5-trimethylsilylmethyl-5H-dibenzo[a,d]cyclohepten-5-ol, respectively.

Step b)

10-(2-dimethylaminoethyl)-10,11-dihydro-5-methylene-5H-dibenzo[a,d]cycloheptene maleate.

A suspension of 24 g. (0.1 mole) of sodium hydride in 200 ml. of tetrahydrofuran is cooled to 0° C and is added to a solution of 36.7 g. (0.1 mole) 10-(2-dimethylaminoethyl)-10,11-dihydro-5-trimethylsilyl-methyl-5H-dibenzo[a,d]cyclohepten-5-ol in 200 ml. of tetrahydrofuran while maintaining temperature at 0° C. After the addition is complete, the mixture is heated to reflux for 5 hours. The resultant mixture is cooled to 0° C. and treated with 15 ml. of methanol to remove any unreacted sodium hydride and the solvents are removed in vacuo. The oily residue is distilled at 140° C./0.5 mm. and the distillate is dissolved in ethanol and treated with maleic acid. The precipitate is filtered and recyrstallized from diethylether-ethanol 1:1, to give 10-(2-dimethylaminoethyl)-10,11-dihydro-5-methylene-5H-dibenzo[a,d]cycloheptene maleate, m.p. 171 to 172° C.

Following the above procedure and using in place of 10-(2-dimethylaminoethyl)-10,11-dihydro-5-trimethylsilylmethyl-5H-dibenzo[a,d]cyclohepten-5-ol an equivalent amount of
- a. 10-(2-dimethylaminoethyl)-10,11-dihydro-2,7-difluoro-5-trimethylsilylmethyl-5H-dibenzo[a,d]cyclohepten-5-ol,
- b. 10-(2-dimethylaminoethyl)-10,11-dihydro-7-fluoro-5-trimethylsilylmethyl-5H-dibenzo[a,d]cyclohepten-5-ol,
- c. 10-(2-dimethylaminoethyl)-10,11-dihydro-8-fluoro-5-trimethylsilylmethyl-5H-dibenzo[a,d]cyclohepten-5-ol,
- d. 10-(2-diethylaminoethyl)-10,11-dihydro-5-trimethylsilylmethyl-5H-dibenzo[a,d]cyclohepten-5-ol, or
- e. 10-(2-dimethylaminoethyl)-10,11-dihydro-2-fluoro-5-trimethylsilylmethyl-5H-dibenzo[a,d]cyclohepten-5-ol, there is obtained
- a. 10-(2-dimethylaminoethyl)-10,11-dihydro-2,7-difluoro-5-methylene-5H-dibenzo[a,d]cycloheptene maleate,
- b. 10-(2-dimethylaminoethyl)-10,11-dihydro-7-fluoro-5-methylene-5H-dibenzo[a,d]cycloheptene maleate,
- c. 10-(2-dimethylaminoethyl)-10,11-dihydro-8-fluoro-5-methylene-5H-dibenzo[a,d]cycloheptene maleate,
- d. 10-(2-diethylaminoethyl)-10,11-dihydro-5-methylene-5H-dibenzo[a,d]cycloheptene maleate, or
- e. 10-(2-dimethylaminoethyl)-10,11-dihydro-2-fluoro-5-methylene-5H-dibenzo [a,d]cycloheptene maleate, respectively.

EXAMPLE 6

Step a.$_1$.

10-(2-dimethylaminoethyl)-10,11-dihydro-5-phenylthiomethyl-5H-dibenzo[a,d]cyclohepten-5-benzoate.

A solution of phenylthiomethyllithium (~0.5 m) is prepared by reacting 6.22 g. (0.05 mole) of thioanisole in 72 ml. of dry tetrahydrofuran with 22.0 ml. of 2.3M solution of phenyllithium for 15 hours at room temperature under nitrogen. A solution of 1.94 g. (0.007 mole) of 10-(2-dimethylaminoethyl)-10,11-dihydro-5H-dibenzo[a,d]cyclohepten-5-one in 40 ml. of tetrahydrofuran is then added to a 42 ml. (~0.021 mole) portion of the phenylthiomethyllithium with ice-cooling. Stirring is initiated at room temperature for 24 hours. The resulting 10-(2-dimethylaminoethyl)-10,11-dihydro-5-phenylthiomethyl-5H-dibenzo[a,d]cycloheptene-5-ol is then poured onto a saturated salt solution and extracted with ether and the ether solution dried over anhydrous magnesium sulfate. The ether solution is cooled in ice and treated with 4.5 ml. of n-butyllithium in hexane (1.54 M solution 0.007 ice and 0.96 ml. (0.008 mole) of benzoyl chloride in 10 ml. ether is then added. The mixture is stirred for 3 hours at room temperature, diluted with ether and washed with water, saturated with sodium bicarbonate and then washed again with water. The ether is dried over anhydrous magnesium sulfate, filtered and evaporated and the residue purified to give 10-(2-dimethylaminoethyl)-10,11-dihydro-5-phenylthiomethyl-5H-dibenzo[a,d]cyclohepten-5-benzoate.

Following the above procedure and using in place of 10-(2-dimethylaminoethyl)-10,11-dihydro-5H-dibenzo[a,d]cyclohepten-5-one an equivalent amount of
- a. 10-(2-dimethylaminoethyl)-10,11-dihydro-2,7-difluoro-5H-dibenzo[a,d]cyclohepten-5-one,
- b. 10-(2-dimethylaminoethyl)-10,11-dihydro-7-fluoro-5H-dibenzo[a,d]cyclohepten-5-one, c. 10-(2-dimethylaminoethyl)-10,11-dihydro-8-fluoro-5H-dibenzo[a,d]cyclohepten-5-one,
d. 10-(2-diethylaminoethyl)-10,11-dihydro-5H-dibenzo[a,d]cyclohepten-5-one, or
e. 10-(2-dimethylaminoethyl)-10,11-dihydro-2-fluoro-5H-dibenzo[a,d]cyclohepten-5-one, there is obtained
  a. 10-(2-dimethylaminoethyl)-10,11-dihydro-2,7-difluoro-5-phenylthiomethyl-5H-dibenzo[a,d]cyclohepten-5-benzoate,
  b. 10-(2-dimethylaminoethyl)-10,11-dihydro-7-fluoro-5-phenylthiomethyl-5H-dibenzo[a,d]cyclohepten-5-benzoate,
  c. 10-(2-dimethylaminoethyl)-10,11-dihydro-8-fluoro-5-phenylthiomethyl-5H-dibenzo[a,d]cyclohepten-5-benzoate,
  d. 10-(2-diethylaminoethyl)-10,11-dihydro-5-phenylthiomethyl-5H-dibenzo[a,d]cyclohepten-5-benzoate, or
  e. 10-(2-dimethylaminoethyl)-10,11-dihydro-2-fluoro-5-phenylthiomethyl-5H-dibenzo[a,d]cyclohepten-5-benzoate, through the corresponding intermediates
  a. 10-(2-dimethylaminoethyl)-10,11-dihydro-2,7-difluoro-5-phenylthiomethyl-5H-dibenzo[a,d]cyclohepten-5-ol,
  b. 10-(2-dimethylaminoethyl)-10,11-dihydro-7-fluoro-5-phenylthiomethyl-5H-dibenzo[a,d]cyclohepten-5-ol,
  c. 10-(2-dimethylaminoethyl)-10,11-dihydro-8-fluoro-5-phenylthiomethyl-5H-dibenzo[a,d]cyclohepten-5-ol,
  d. 10-(2-diethylaminoethyl)-10,11-dihydro-5-phenylthiomethyl-5H-dibenzo[a,d]cyclohepten-5-ol, or
  e. 10-(2-dimethylaminoethyl)-10,11-dihydro-2-fluoro-5-phenylthiomethyl-5H-dibenzo[a,d]cyclohepten-5-ol, respectively.

Step b.
10-(2-dimethylaminoethyl)-10,11-dihydro-5-methylene-5H-dibenzo[a,d]cycloheptene maleate.

To a refluxing solution of 0.28 g. of lithium (0.04 mole) in 150 ml. liquid ammonia under nitrogen there is added a solution of 2.29 g. of 10-(2-dimethylaminoethyl)-10,11-dihydro-5-phenylthiomethyl-5H-dibenzo[a,d]cyclohepten-5-benzoate (0.004 mole) in 50 ml. ether over about 30 minutes. Reflux is continued for an additional 30 minutes and then the mixture is hydrolyzed by the addition of ammonium chloride in small portions. The ammonia is evaporated while ether is added in small portions. The resulting mixture is added to water, the layers separated and the ether washed with 1N sodium hydroxide and water, dried over anhydrous magnesium sulfate, filtered and evaporated. The residue is dissolved in ethanol and treated with maleic acid. The resulting precipitate is filtered and recrystallized from diethylether-ethanol 1:1 to give 10-(2-dimethylaminoethyl)-10,11-dihydro-5-methylene-5H-dibenzo[a,d]cycloheptene maleate, m.p. 171° to 172° C.

Following the above procedure and using in place of 10-(2-dimethyl)aminoethyl)-10,11-dihydro-5-phenylthiomethyl-5H-dibenzo[a,d]cyclohepten-5-benzoate an equivalent amount of
  a. 10-(2-dimethylaminoethyl)-10,11-dihydro-2,7-difluoro-5-phenylthiomethyl-5H-dibenzo[a,d]cyclohepten-5-benzoate,
  b. 10-(2-dimethylaminoethyl)-10,11-dihydro-7-fluoro-5-phenylthiomethyl-5H-dibenzo[a,d]cyclohepten-5-benzoate,
  c. 10-(2-dimethylaminoethyl)-10,11-dihydro-8-fluoro-5-phenylthiomethyl-5H-dibenzo[a,d]cyclohepten-5-benzoate,
  d. 10-(2-diethylaminoethyl)-10,11-dihydro-5-phenylthiomethyl-5H-dibenzo[a,d]cyclohepten-5-benzoate, or
  e. 10-(2-dimethylaminoethyl)-10,11-dihydro-2-fluoro-5-phenylthiomethyl-5H-dibenzo[a,d]cyclohepten-5-benzoate, there is obtained
  a. 10-(2-dimethylaminoethyl)-10,11-dihydro-2,7-difluoro-5-methylene-5H-dibenzo[a,d]cycloheptene maleate,
  b. 10-(2-dimethylaminoethyl)-10,11-dihydro-7-fluoro-5-methylene-5H-dibenzo[a,d]cycloheptene maleate,
  c. 10-(2-dimethylaminoethyl)-10,11-dihydro-8-fluoro-5-methylene-5H-dibenzo[a,d]cycloheptene maleate,
  d. 10-(2-diethylaminoethyl)-10,11-dihydro-5-methylene-5H-dibenzo[a,d]cycloheptene maleate, or
  e. 10-(2-dimethylaminoethyl)-10,11-dihydro-2-fluoro-5-methylene-5H-dibenzo[a,d]cycloheptene maleate, respectively.

EXAMPLE 7

Step a.
10-(2-dimethylaminoethyl)-10,11-dihydrospiro[dibenzo[a,d]cyclohepten-5,2'-oxirane].

A mixture of 27.6 g. of sodium hydride (0.12 mole) and 26.4 g. trimethyloxosulfonium iodide is treated slowly with 200 ml. dimethylsulfoxide. Stirring is initiated and a vigorous evolution of $H_2$ ensued, which stopped after the addition is complete. The resulting mixture is then treated with 27.9 g. (0.1 mole) of 10-(2-dimethylaminoethyl)-10,11-dihydro-5H-dibenzo[a,d]cyclohepten-5-one in 50 ml. dimethylsulfoxide. The reaction mixture is stirred for 15 minutes at room temperature and then at 50° C. for 1 hour. The reaction mixture is then cooled and treated with a three fold excess of ice water and extracted with ether. The ether is washed with water, dried over anhydrous magnesium sulfate, filtered and evaporated. The residue is purified to give 10-(2-dimethylaminoethyl)-10,11-dihydrospiro[dibenzo]cyclohepten-5,2'-oxirane].

Following the above procedure and using in place of 10-(2-dimethylaminoethyl)-10,11-dihydro-5H-dibenzo[a,d]cyclohepten-5-one an equivalent amount of
  a. 10-(2-dimethylaminoethyl)-10,11-dihydro-2,7-difluoro-5H-dibenzo[a,d]cyclohepten-5-one hydrochloride,
  b. 10-(2-dimethylaminoethyl)-10,11-dihydro-7-fluoro-5H-dibenzo[a,d]cyclohepten-5-one hydrochloride,
  c. 10-(2-dimethylaminoethyl)-10,11-dihydro-8-fluoro-5H-dibenzo[a,d]cyclohepten-5-one hydrochloride,
  d. 10-(2-diethylaminoethyl)-10,11-dihydro-dibenzo[a,d]cyclohepten-5-one hydrochloride, or
  e. 10-(2-dimethylaminoethyl)-10,11-dihydro-2-fluoro-5H-dibenzo[a,d]cyclohepten-5-one hydrochloride, there is obtained
  a. 10-(2-dimethylaminoethyl)-2,7-difluoro-10,11-dihydrospiro[dibenzo[a,d]cyclohepten-5,2'-oxirane],
  b. 10-(2-dimethylaminoethyl)-7-fluoro-10,11-dihydrospiro[dibenzo[a,d]cyclohepten-5,2'-oxirane], c. 10-(2-dimethylaminoethyl)-8-fluoro-10,11-dihydrospiro[dibenzo[a,d]cyclohepten-5,2'-oxirane]
d. 10-(2-diethylaminoethyl)-10,11-dihydrospiro[dibenzo[a,d]cyclohepten-5,2'-oxirane], or
e. 10-(2-dimethylaminoethyl)-2-fluoro-10,11-dihydrospiro[dibenzo[a,d]cyclohepten-5,2'-oxirane], respectively.

Step b.

10-(2-dimethylaminoethyl)-10,11-dihydro-5-methylene-5H-dibenzo[a,d]cycloheptene maleate.

A mixture of 29.3 g. of 10-(2-dimethylaminoethyl)-10,11-dihydrospiro[dibenzo[a,d]cyclohepten-5,2'-oxirane](0.1 mole) and 26.2 g. of triphenylphosphine is heated at 180° C. for 5 hours. The mixture is cooled and treated with water and ether. The layers are separated and the ether washed with water, dried over anhydrous magnesium sulfate, filtered and evaporated. The residue is distilled at 140° C./0.5 mm. and the distillate is dissolved in ethanol and treated with maleic acid. The precipitate is filtered and recrystallized from diethylether-ethanol 1:1 to give 10-(2-dimethylaminoethyl)-10,11-dihydro-5-methylene-5H-dibenzo[a,d]cycloheptene maleate, m.p. 171°–172° C.

Following the above procedure and using a place of 10-(2-dimethylaminoethyl)-10,11-dihydrospiro[dibenzo[a,d]cyclohepten-5,2'-oxirane] an equivalent amount of
a. 10-(2-dimethylaminoethyl)-2,7-difluoro-10,11-dihydrospiro[dibenzo[a,d]cyclohepten-5,2'-oxirane]
b. 10-(2-dimethylaminoethyl)-7-fluoro-10,11-dihydrospiro[dibenzo[a,d]cyclohepten-5,2'oxirane],
c. 10-(2-dimethylaminoethyl)-8-fluoro-10,11-dihydrospiro[dibenzo[a,d]cyclohepten-5,2'-oxirane],
d. 10-(2-diethylaminoethyl)-10,11-dihydrospiro[dibenzo[a,d]cyclohepten-4,2'-oxirane], or
e. 10-(2-dimethylaminoethyl)-2-fluoro-10,11-dihydrospiro[dibenzo[a,d]cyclohepten-5,2'-oxirane],
there is obtained
a. 10-(2-dimethylaminoethyl)-10,11-dihydro-2,7-difluoro-5-methylene-5H-dibenzo[a,d]cycloheptene maleate,
b. 10-(2-dimethylaminoethyl)-10,11-dihydro-7-fluoro-5-methylene-5H-dibenzo[a,d]cycloheptene maleate,
c. 10-(2-dimethylaminoethyl)-10,11-dihydro-8-fluoro-5-methylene-5H-dibenzo[a,d]cycloheptene maleate
d. 10-(2-diethylaminoethyl)-10,11-dihydro-5-methylene-5H-dibenzo[a,d]cycloheptene maleate, or
e. 10-(2-dimethylaminoethyl)-10,11-dihydro-2-fluoro-5-methylene-5H-dibenzo[a,d]cycloheptene maleate, respectively.

EXAMPLE 8

10-(2-dimethylaminoethyl)-10,11-dihydro-5-methylene-5H-dibenzo[a,d]cycloheptene maleate.

A mixture of 2.3 g. (0.1 mole) of sodium hydride and 50 ml. dimethylsulfoxide are heated at 75°–80° C. until hydrogen evolution has ceased. The mixture is cooled in an ice-bath and 35.7 g. (0.1 mole) of methyl triphenyl phosphonium bromide in 100 ml. dimethyl sulfoxide is added. The resulting solution is stirred at room temperature for 10 minutes. Then 27.9 g. (0.1 mole) of 10-(2-dimethylaminoethyl)-10,11-dihydro-5H-dibenzo[a,d]cyclohepten-5-one in 25 ml. of dimethyl sulfoxide is added and the mixture is stirred for one hour at room temperature then treated with a three fold excess of ice-water and extracted with ether. The ether extract is washed with water, dried over anhydrous magnesium sulfate, filtered and evaporated. The residue is distilled at 140° C./0.5 mm. and the distillate is dissolved in ethanol and treated with maleic acid. The precipitate is filtered and recrystallized from diethylether-ethanol 1:1 to give 10-(2-dimethylaminoethyl)-10,11-dihydro-5-methylene-5H-dibenzo[a,d]cycloheptene maleate, m.p. 171°–172° C.

Following the above procedure and using in place of 10-(2-dimethylaminoethyl)-10,11-dihydro-5H-dibenzo[a,d]cyclohepten-5-one, an equivalent amount of
a. 10-(2-dimethylaminoethyl)-10,11-dihydro-2,7-difluoro-5H-dibenzo[a,d]cyclohepten-5-one,
b. 10-(2-dimethylaminoethyl)-10,11-dihydro-7-fluoro-5H-dibenzo[a,d]cyclohepten-5-one,
c. 10-(2-dimethylaminoethyl)-10,11-dihydro-8-fluoro-5H-dibenzo[a,d]cyclohepten-5-one,
d. 10-(2-diethylaminoethyl)-10,11-dihydro-5H-dibenzo[a,d]cyclohepten-5-one, or
e. 10-(2-dimethylaminoethyl)-10,11-dihydro-2-fluoro-5H-dibenzo[a,d]-cyclohepten-5-one,
there is obtained
a. 10-(2-dimethylaminoethyl)-10,11-dihydro-2,7-difluoro-5-methylene-5H-dibenzo[a,d]cycloheptene maleate,
b. 10-(2-dimethylaminoethyl)-10,11-dihydro-7-fluoro-5-methylene-5H-dibenzo[a,d]cycloheptene maleate,
c. 10-(2-dimethylaminoethyl)-10,11-dihydro-8-fluoro-5-methylene-5H-dibenzo[a,d]cycloheptene maleate,
d. 10-(2-diethylaminoethyl)-10,11-dihydro-5H-methylene-5H-dibenzo[a,d]cycloheptene maleate, or
e. 10-(2-dimethylaminoethyl)-10,11-dihydro-2-fluoro-5-methylene-5H-dibenzo[a,d]cycloheptene maleate, respectively.

EXAMPLE 9

2-($\beta$-[2-dimethylaminoethyl]phenethyl)benzoic acid.

To a well stirred suspension of 45 g. of zinc dust, 90 ml. of concentrated ammonium hydroxide, 45 ml. of water and 2 ml. of cupric sulfate maintained at 80° C. there is added 14.75 g. (0.05 mole) of 3-(2-dimethylaminoethyl)-3,4-dihydro-3,4-dihydro-3-phenylisocoumarin in 50 ml. ethanol for about 30 minutes. The resulting mixture is heated at 85° C. for 30 hours while a slow stream of ammonia is passed through. The mixture is filtered while under heat and the solids washed throughly with 100 ml. of hot ammonium hydroxide. The combined filtrates are cooled and carefully acidified with concentrated hydrochloric acid to give 2-($\beta$-[-2-dimethylaminoethyl]phenethyl]benzoic acid, m.p. 152° to 154° C.

Following the above procedure and using in place of 3-(2-dimethylaminoethyl)-3,4-dihydro-3-phenylisocoumarin an equivalent amount of
a. 3-(4-fluorophenyl)-3-(2-dimethylaminoethyl)-3,4-dihydro-6-fluoro isocoumarin,
b. 3-(4-fluorophenyl)-3-(2-dimethylaminoethyl)-3,4-dihydro isocoumarin,
c. 3-(3-fluorophenyl)-3-(2-dimethylaminoethyl)-3,4-dihydro isocoumarin, or d. 3-(2-diethylaminoethyl)-3,4-dihydro-3-phenyl isocoumarin, or
e. 3-(2-dimethylaminoethyl)-3,4-dihydro-6-fluoro isocoumarin, the following intermediates are obtained,
  a. 4-fluoro-2-(β-[2-dimethylaminoethyl]-p-fluorophenethyl)benzoic acid hydrochloride,
  b. 2-(β-[2-dimethylaminoethyl]-p-fluorophenethyl)benzoic acid hydrochloride,
  c. 2-(β-[2-dimethylaminoethyl]-m-fluorophenethyl)benzoic acid hydrochloride,
  d. 2-(β-[2-diethylaminoethyl]phenethyl)benzoic acid hydrochloride, or
  e. 4-fluoro-2-(β-[2-dimethylaminoethyl]phenethyl)benzoic acid hydrochloride, respectively.

EXAMPLE 10

2-(β-[2-dimethylaminoethyl]phenethyl)benzoic acid ethyl ester.

A solution of 29.7 g. (0.1 mole) of 2-(β-[2-dimethylaminoethyl]phenethyl)benzoic acid in 200 ml. of ethanol is saturated with gaseous hydrochloride, and the resulting mixture is refluxed for 18 hours. The solvent is removed in vacuo and the residue is partitioned between ether and 2N sodium hydroxide. The ether extract is dried and evaporated in vacuo to give 2-(β-[2-dimethylaminoethyl]phenethyl)benzoic acid ethyl ester.

Following the above procedure and using in place of 2-(β-[2-dimethylaminoethyl]phenethyl)benzoic acid an equivalent amount of a. 4-fluoro-2-(β-[2dimethylaminoethyl]-p-fluorophenethyl)benzoic acid,
  b. 2-(β-[2-dimethylaminoethyl]-p-fluorophenethyl)benzoic acid
  c. 2-(β-[2-dimethylaminoethyl]-m-fluorophenethyl)benzoic acid,
  d. 2-(β-[2-diethylaminoethyl]phenethyl)benzoic acid, or
  e. 4-fluoro-2-(β-[2-dimethylaminoethyl]phenethyl)benzoic acid, the following intermediates are obtained,
  a. 4-fluoro-2-(β-[2-dimethylaminoethyl]-p-fluorophenethyl)benzoic acid ethyl ester,
  b. 2-(β-[2-dimethylaminoethyl]-p-fluorophenethyl)benzoic acid ethyl ester,
  c. 2-(β-[2-dimethylaminoethyl]-m-fluorophenethyl)benzoic acid ethyl ester, or
  d. 2-(β-[2-diethylaminoethyl]phenethyl)benzoic acid ethyl ester, or
  e. 4-fluoro-2-(β-[2-dimethylaminoethyl]phenethyl)benzoic acid ethyl ester,
respectively.

EXAMPLE 11

10-(2-dimethylaminoethyl)-10,11-dihydro-5-methylene-5H-dibenzo[a,d]cycloheptene

To a mixture of 5 g. of 10-(2-dimethylaminoethyl)-10,11-dihydro-5-methylene-5H-dibenzo[a,d]cycloheptene maleate in 150 ml. of methylene chloride there is added 50 ml. of 2N-sodium hydroxide, the mixture is shaken, the methylene chloride is dried, filtered and evaporated in vacuo to give 10-(2-dimethylaminoethyl)-10,11-dihydro-5-methylene-5H-dibenzo[a,d]cycloheptene.

Following the above procedure and using in place of 10-(2-dimethylaminoethyl)-10,11-dihydro-5-methylene-5H-dibenzo[a,d]cycloheptene maleate an equivalent amount of
  a. 10-(2-dimethylaminoethyl)-10,11-dihydro-2,7-difluoro-5-methylene-5H-dibenzo[a,d]cycloheptene maleate, or
  b. 10-(2-dimethylaminoethyl)-10,11-dihydro-7-fluoro-5-methylene-5H-dibenzo[a,d]cycloheptene maleate,
  c. 10-(2-dimethylaminoethyl)-10,11-dihydro-8-fluoro-5-methylene-5H-dibenzo[a,d]cycloheptene maleate,
  d. 10-(2-diethylaminoethyl)-10,11-dihydro-5-methylene-5H-dibenzo[a,d]cycloheptene maleate, or
  e. 10-(2-dimethylaminoethyl)-10,11-dihydro-2-fluoro-5-methylene-5H-dibenzo[a,d]cycloheptene maleate, there is obtained
  a. 10-(2-dimethylaminoethyl)-10,11-dihydro-2,7-difluoro-5-methylene-5H-dibenzo[a,d]cycloheptene,
  b. 10-(2-dimethylaminoethyl)-10,11-dihydro-7-fluoro-5-methylene-5H-dibenzo[a,d]cycloheptene,
  c. 10-(2-dimethylaminoethyl)-10,11-dihydro-8-fluoro-5-methylene-5H-dibenzo[a,d]cycloheptene,
  d. 10-(2-diethylaminoethyl)-10,11-dihydro-5-methylene-5H-dibenzo[a,d]cycloheptene, or
  e. 10-(2-dimethylaminoethyl)-10,11-dihydro-2-fluoro-5-methylene-5H-dibenzo[a,d]cycloheptene, respectively.

EXAMPLE 12

10-(2-methylaminoethyl)-10,11-dihydro-5-methylene-5H-dibenzo[a,d]cycloheptene.

A mixture of 15.2 g. (0.055 mole) of 10-(2-dimethylaminoethyl)-10,11-dihydro-5-methylene-5H-dibenzo[a,d]cycloheptene and 23.6 g. (0.218 mole) of ethylchloroformate in 125 ml. of toluene is refluxed under a nitrogen atmosphere for 18 hours. The excess solvent and reagent is removed by evaporation in vacuo. The resulting oil product is dissolved in a solution of 175 ml. of ethanol, 17 ml of water and 35 g. (0.625 mole) of potassium hydroxide and refluxed for 10 hours. The solvents are removed in vacuo and the resulting layers are separated between ether and water. The ether is then extracted twice with 2N hydrochloric acid and the resulting aqueous acid is then made basic and extracted with ether. The excess solvent is then dried and evaporated and the resulting oil is dissolved in isopropyl alcohol and treated with hydrochloric gas. The residue is then filtered and recrystallized from isopropyl alcohol to give 10-(2-methylaminoethyl)-10,11-dihydro-5-methylene-5H-dibenzo[a,d]cycloheptene hydrochloride, m.p. 176°–177° C.

Following the above procedure and using in place of 10-(2-dimethylaminoethyl)-10,11-dihydro-5-methylene-5H-dibenzo[a,d]cycloheptene, an equivalent amount of
  a. 10-(2-dimethylaminoethyl)-10,11-dihydro-2,7-difluoro-5H-dibenzo[a,d]cycloheptene
  b. 10-(2-dimethylaminoethyl)-10,11-dihydro-7-fluoro-5H-dibenzo[a,d]cycloheptene
  c. 10-(2-dimethylaminoethyl)-10,11-dihydro-8-fluoro-5H-dibenzo[a,d]cycloheptene
  d. 10-(2-dimethylaminoethyl)-10,11-dihydro-2-fluoro-5H-dibenzo[a,d]cycloheptene, or there is obtained the hydrochloride salt of
a. 10-(2-methylaminoethyl)-10,11-dihydro-2,7-difluoro-5H-dibenzo[a,d]cycloheptene
b. 10-(2-methylaminoethyl)-10,11-dihydro-7-fluoro-5H-dibenzo[a,d]cycloheptene.
c. 10-(2-methylaminoethyl)-10,11-dihydro-8-fluoro-5H-dibenzo[a,d]cycloheptene, or
d. 10-(2-methylaminoethyl)-10,11-dihydro-2-fluoro-5H-dibenzo[a,d]cycloheptene, respectively.

EXAMPLES 13 and 14

Tablets and Capsules Suitable for Oral Administration

Tablets and capsules containing the ingredients indicated below may be prepared by conventional techniques and are useful as anti-depressants at a dose of one tablet or capsule 2 to 4 times a day.

| Ingredients | Weight (mg) tablet | capsule |
|---|---|---|
| 10-(2-dimethylaminoethyl)-10,11-dihydro-5-methylene-5H-dibenzo[a,d]cycloheptene maleate | 25 | 25 |
| tragacanth | 10 | — |
| lactose | 222.5 | 275 |
| corn starch | 25 | |
| talcum | 15 | |
| magnesium stearate | 2.5 | |

EXAMPLES 15 and 16

Sterile Suspension for Injection and Oral Liquid Suspension

The following pharmaceutical compositions are formulated with the indicated amount of active agent using conventional techniques. The injectable suspension and the oral liquid suspension represent formulations useful as unit doses and may be administered as anti-depressants. The injectable suspension is suitable for administration once a day where as the oral liquid suspension is suitably administered 2 to 4 times per day for this purpose.

| Ingredients | Weight (mg) Sterile Injectable Suspension | Oral Liquid Suspension |
|---|---|---|
| 10-(2-dimethylaminoethyl)-10,11-dihydro-5-methylene-5H-dibenzo[a,d]cycloheptene maleate | 25 | 25 |
| sodium carboxy methyl cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | — | 5 |
| sorbitol solution, 70%, U.S.P. | — | 2,500 |
| buffer agent to adjust pH for desired stability | q.s. | q.s. |
| water | q.s. for injection, q.s. to 1 ml. | q.s. to 5 ml. |

What is claimed is:
1. A compound of the formula

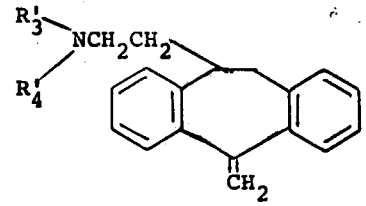

where
R'$_3$ and R'$_4$ are independently lower alkyl having 1 to 2 carbon atoms, or one of R'$_3$ and R'$_4$ is hydrogen and the other is methyl,
or a pharmaceutically acceptable acid addition salt thereof.

2. The compound of claim 1 which is 10-(2-dimethylaminoethyl)-10,11-dihydro-5-methylene-5H-dibenzo[a,d]cycloheptene.

3. The compound of claim 1 which is 10-(2-dimethylaminoethyl)-10,11-dihydro-5-methylene-5H-dibenzo[a,d]cycloheptene maleate.

4. The compound of claim 1 which is 10-(2-methylaminoethyl)-10,11-dihydro-5-methylene-5H-dibenzo[a,d]cycloheptene hydrochloride.

5. The compound of claim 1 which is 10-(2-methylaminoethyl)10,11-dihydro-5-methylene-5H-dibenzo[a,d]cycloheptene.

* * * * *